United States Patent [19]
Kline et al.

[11] Patent Number: 5,542,942
[45] Date of Patent: Aug. 6, 1996

[54] ABSORBENT ARTICLE WITH IMPROVED ELASTICIZED WAISTBAND

[75] Inventors: Mark J. Kline, Cincinnati; Donald C. Roe, West Chester; Dean J. Daniels; James E. Zorb, both of Cincinnati; Jerry L. Dragoo, Fairfield, all of Ohio

[73] Assignee: The Procter & Gamble Company, Cincinnati, Ohio

[21] Appl. No.: 310,599

[22] Filed: Sep. 22, 1994

[51] Int. Cl.⁶ ........................................... A61F 13/15
[52] U.S. Cl. ................ 604/385.2; 604/386; 604/387; 604/391
[58] Field of Search ..................... 604/358, 373, 604/385.1, 385.2, 386, 387, 389, 391, 392, 394, 396, 397, 402

[56] References Cited

U.S. PATENT DOCUMENTS

| | | | |
|---|---|---|---|
| 3,610,244 | 10/1971 | Jones, Sr. . | |
| 4,381,781 | 5/1983 | Sciaraffa et al. | 604/372 |
| 4,617,022 | 10/1986 | Pigneul et al. | 604/391 |
| 4,681,580 | 7/1987 | Reising et al. | 604/385 A |
| 4,685,916 | 8/1987 | Enloe | 604/385 A |
| 4,701,175 | 10/1987 | Boland et al. | 604/385 A |
| 4,808,176 | 2/1989 | Kielpikowski | 604/385.2 |
| 4,808,252 | 2/1989 | Lash | 156/73.1 |
| 4,857,067 | 8/1989 | Wood et al. | 604/389 |
| 4,872,871 | 10/1989 | Proxmire et al. | 604/394 |
| 4,891,258 | 1/1990 | Fahrenkrug | 428/138 |
| 4,895,568 | 1/1990 | Enloe | 604/385.2 |
| 4,923,456 | 5/1990 | Proxmire | 604/391 |
| 4,968,313 | 11/1990 | Sabee | 604/385.2 |
| 4,998,929 | 3/1991 | Bjorksund et al. | 604/385.2 |
| 5,004,466 | 4/1991 | Uda et al. | 604/385.2 |
| 5,019,066 | 5/1991 | Freeland et al. | 604/385.2 |
| 5,019,073 | 5/1991 | Roessler et al. | 604/391 |
| 5,032,119 | 7/1991 | Hookano | 604/385.1 |
| 5,034,008 | 7/1991 | Breitkopf | 604/385.2 |
| 5,057,097 | 10/1991 | Gesp | 604/389 |
| 5,061,262 | 10/1991 | Chen et al. | 604/389 |
| 5,100,400 | 3/1992 | Mody et al. | 604/391 |
| 5,151,092 | 9/1992 | Buell et al. | 604/385.2 |

(List continued on next page.)

FOREIGN PATENT DOCUMENTS

| | | | |
|---|---|---|---|
| 0211197 | 2/1987 | European Pat. Off. . | |
| 0352208 | 1/1990 | European Pat. Off. | 604/385.2 |
| 0362094 | 4/1990 | European Pat. Off. . | |

(List continued on next page.)

*Primary Examiner*—John G. Weiss
*Assistant Examiner*—Mark O. Polutta
*Attorney, Agent, or Firm*—David M. Weirich; Steven W. Miller; Jacobus G. Rasser

[57] ABSTRACT

Absorbent articles to be fitted to wearers, such as disposable diapers, incontinence briefs, diaper holders and the like with improved fastening system and waistband features that provide sustained dynamic fit about the waist of a wearer as well as improved containment characteristics. The absorbent article having a longitudinal centerline, a longitudinal direction which is the direction parallel to said longitudinal centerline, a lateral centerline, a lateral direction which is the direction parallel to said lateral centerline, a first waist region, a first waist feature positioned in said first waist region and being elastically extensible in said lateral direction, a second waist region longitudinally opposed to said first waist region, a first end edge, a second end edge, an inner surface and an outer surface, the absorbent article comprising a containment assembly having a pair of longitudinal edges; a fastening system including a pair of engaging components disposed in said second waist region; and a landing component disposed on said outer surface of the absorbent article in said first waist region coincident with said first waist feature, said landing component being engageable with said engaging components; said landing component being elastically extensible in at least said lateral direction, and at least a portion of said landing component being intermediate said engaging components when said engaging components are engaged with said landing component such that said first waist region and said landing component are activated when the absorbent article is fitted to said wearer.

9 Claims, 3 Drawing Sheets

U.S. PATENT DOCUMENTS

| | | | |
|---|---|---|---|
| 5,242,436 | 9/1993 | Weil et al. | 604/385.2 |
| 5,295,986 | 3/1994 | Zehner et al. | 604/385.1 |
| 5,318,555 | 6/1994 | Siebers et al. | 604/390 |
| 5,330,458 | 7/1994 | Buell et al. | 604/385.1 |
| 5,368,584 | 11/1994 | Clear et al. | 604/385.2 |
| 5,370,634 | 12/1994 | Ando et al. | 604/385.1 |

FOREIGN PATENT DOCUMENTS

| | | | |
|---|---|---|---|
| 2335165 | 12/1975 | France . | |
| 2108823 | 5/1983 | United Kingdom | A41B 13/02 |
| 2185176 | 7/1987 | United Kingdom | A41B 13/02 |
| 2244422 | 12/1991 | United Kingdom . | |

ABSORBENT ARTICLE WITH IMPROVED ELASTICIZED WAISTBAND

FIELD OF THE INVENTION

The present invention relates to absorbent articles such as diapers, incontinence briefs, diaper holders, training pants, and the like, and more particularly to absorbent articles having an elastically extensible waistbands.

BACKGROUND OF THE INVENTION

Infants and other incontinent individuals wear absorbent articles such as diapers to receive and contain urine and other body exudates. Absorbent articles function both to contain the discharged materials and to isolate the materials from the body of the wearer and from the wearer's garments and bed clothing. Disposable absorbent articles having many different designs are known in the art. For example, Re. U.S. Pat. No. 26,152 entitled "Disposable Diaper" issued to Duncan and Baker on Jan. 31, 1967, describes a disposable diaper which has achieved wide acceptance and commercial success. U.S. Pat. No. 3,860,003, entitled "Contractible Side Portions For Disposable Diaper", issued to Buell on Jan. 14, 1975, describes an improved disposable diaper having a elasticized leg cuff that has also achieved wide acceptance and commercial success.

However, absorbent articles have a tendency to sag or gap away from and to slip down the body of the wearer during use. This sagging, gapping and slipping is caused by the wearer as the wearer moves, breathes and changes positions, by the downward forces generated when the absorbent article is loaded with body exudates, and by the deformation of the materials of the absorbent article when subjected to such forces. This sagging, gapping and slipping of the absorbent article can lead to premature leakage and poor fit of the absorbent article especially in the waist and the leg regions.

In order to more snugly fit absorbent articles about the waist of the wearer, certain commercially available absorbent articles have been provided with elasticized waistbands and improved fastening systems. Examples of such disposable diapers are disclosed in U.S. Pat. No. 4,515,595 issued to Kievet and Osterhage on May 7, 1985, U.S. Pat. No. 5,151,092 issued to Buell et al. on Sep. 29, 1992, and U.S. Pat. No. 5,242,436 issued to Weil et al. on Sep. 7, 1993.

Typical elasticized waistbands comprise a precontracted waist feature having an elastic member affixed between the topsheet and the backsheet. The elasticized waistbands are, thus, designed such that the contraction provided by the manufacturer in the waist feature maintains a snug fit about the waist of the wearer during use (i.e. provide sustained dynamic fit). However, precontracted waist features generally add to the cost of the absorbent article due to costly and complex equipment required in the manufacturing process. Further, the fastening systems used in conjunction with precontracted waistbands typically comprise adhesive or mechanical fasteners that join the front and rear of the absorbent article in fastening zones located just below the precontracted waistband (or toward the core of the absorbent article). The waistbands and fastening systems are generally configured in this way to ensure that the fastening system does not interfere with the waistband's ability to provide dynamic fit about the waist of the wearer.

It has been found, though, that absorbent articles having precontracted waistbands and fastening systems as described above still have a tendency to sag, gap or slip during use and the precontracted waistbands have a tendency to rollover or roll-in at the front of the diaper resulting in a lack of fit about the waist of the wearer. Although two-point fastening systems have been developed in order to help prevent some of the sagging, gapping and waistband rollover associated with diapers having fastening systems as described above, the two-point fastening systems tend to be relatively expensive to manufacture. As described in U.S. Pat. No. 5,242,436 issued to Weil et al. on Sep. 7, 1993, the two-point fastening systems generally comprise at least one primary fastening means for providing closure of the diaper about the wearer and a secondary fastening means to provide tension throughout the waistband.

Thus, it would be advantageous to provide an absorbent article having an improved elastically extensible waistband and fastening system that provides better fit, wearer comfort and reduced leakage. It would also be advantageous to provide an absorbent article which has reduced sagging, gapping, rollover, or roll-in at the waist of the diaper as well as reduced overall slipping during use. Further, it would be advantageous to provide the benefits of the currently available waistbands without the costs associated with the complex process of manufacturing precontracted waistbands and the costs associated with two-point fastening systems.

Therefore, it is an object of the present invention to provide an absorbent article having sustained dynamic fit during use.

It is a further object of the present invention to provide an absorbent article that has an elastically extensible waistband and an improved fastening system that is aligned with the elastically extensible waistband to provide sustained dynamic fit and resistance to leakage.

It is still a further object of the present invention to provide an absorbent article that has a fastening system integrated with the waistband to reduce the likelihood of sagging, gapping or rollover in the waist region, and thus, reducing the need for a secondary fastening.

It is yet a further object of the present invention to provide an absorbent article with an elastically extensible, form fitting waistband without the costs or complexities involved with manufacture of the typical precontracted waistbands available to the consumer today.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinence briefs, diaper holders and the like with an improved waistband fastening feature that provides sustained dynamic fit about the waist of the wearer as well as improved containment characteristics. The absorbent article has a first waist region and a second waist region and preferably comprises a containment assembly comprising a liquid pervious topsheet, a liquid impervious backsheet joined with said topsheet, and an absorbent core positioned between said topsheet and said backsheet. The absorbent article further comprises a first waist feature located in the first waist region, the first waist feature being elastically extensible in at least the lateral direction; and a fastening system. The fastening system preferably comprises a pair of engaging components located on opposing side panels; and a landing component located on the outer surface of the absorbent article in the first waist region and coincident with the first waist feature, the landing component being engageable with the engaging components and the landing component being is elastically extensible in at least the lateral direction intermediate the engaging components when the engaging components are engaged with the landing component.

The coincident configuration of the elastically extensible first waist feature and the landing component of the fastening system provides a unique waistband that improves the fit and containment characteristics of the absorbent article. Further, because the landing component is elastically extensible it may be disposed over all or any portion of the first waist feature without reducing the benefits of the waistband. Thus, a landing zone may be provided that permits variable positioning of the engaging elements depending on the size of the wearer.

When the absorbent article of the present invention is fitted to a wearer, the first waist feature is positioned across the front of the wearer. The diaperer then wraps the side panels about the wearer. The elastically extensible side panels will typically be extended and tensioned during this operation. The force applied to extend and tension the side panels is stored as energy in the elastically extensible portion of the side panels until the diaperer releases the force. Typically, the diaperer will release the force applied to the side panels once the diaper has been fastened about the waist of the wearer. Preferably the diaperer utilizes the fastening system to effect closures on each side of the diaper; the engaging components are engaged with the landing component. At least a portion of the energy stored in the elastically extensible portions of the side panels is transferred to the first waist feature when the diaperer releases the tension applied to the side panels. The transfer of energy from the side panels activates the first waist feature causing the first waist feature to hug the waist of the wearer and permitting the waistband to expand and contract with the motions of the wearer. Thus, a novel, cost effective waistband is provided that directs the tensional forces created when fitting the diaper to a wearer through the waistband to improve the sustained dynamic fit of absorbent articles while reducing the likelihood of leaking, gapping or rollover in the waist region of absorbent articles without the cost and manufacturing complexity of two-point fastening systems.

BRIEF DESCRIPTION OF THE DRAWINGS

While the specification concludes with claims particularly pointing out and distinctly claiming the subject matter which is regarded as forming the present invention, it is believed that the invention will be better understood in conjunction with the accompanying drawings, in which:

DETAILED DESCRIPTION OF THE INVENTION

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. A preferred embodiment of a unitary absorbent article comprising the integrated elasticticized waistband and fastening zone of the present invention is the disposable absorbent article shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

Figure 1:
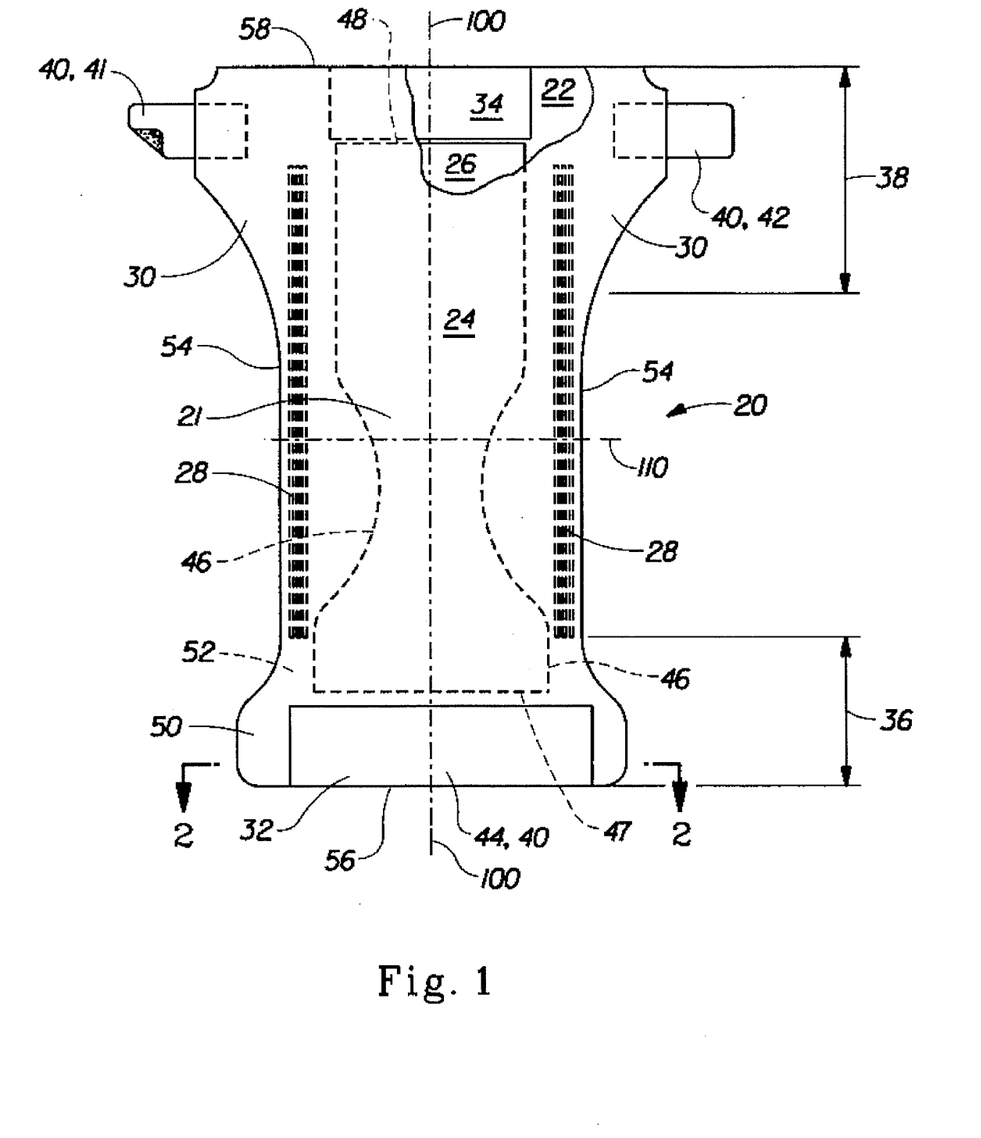
FIG. 1 is a plan view of a disposable diaper embodiment of the present invention having portions cut away to reveal underlying structure, the outer surface of the diaper faces the viewer.

FIG. 1 is a plan view of the diaper 20 of the present invention in its flat-out, uncontracted state (i.e. with elastic induced contraction pulled out) with portions of the structure being cut-away to more clearly show the construction of the diaper 20. As shown in FIG. 1, the diaper 20 preferably comprises a containment assembly 21 comprising a liquid pervious topsheet 22, a liquid impervious backsheet 24 joined to the topsheet 22, and an absorbent core 26 positioned between the topsheet 22 and the backsheet 24. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference. The diaper 20 preferably further comprises a first waist region 36, a second waist region 38, elasticized leg cuffs 28, side panels 30, a first waist feature 32, a second waist feature 34 and a fastening system 40 comprising at least one engaging component 42 and at least one landing component 44.

The diaper 20 is shown in FIG. 1 to have an outer surface 50 (facing the viewer in FIG. 1), an inner surface 52 opposed to the outer surface 50, and a periphery which is defined by the outer perimeter or edges of the diaper 20 having a front waist region end edge 56 and a rear waist region end edge 58, and longitudinal edges 54. The inner surface 52 of the diaper 20 comprises that portion of the diaper 20 which is positioned adjacent to the wearer's body during use (i.e., the inner surface 52 generally is formed by at least a portion of the topsheet 22 and other components joined to the topsheet 22). The outer surface 50 comprises that portion of the diaper 20 which is positioned away from the wearer's body (i.e., the outer surface 50 is generally formed by at least a portion of the backsheet 24 and other components joined to the backsheet 24). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

The diaper 20 also has two centerlines, a longitudinal centerline 100 and a lateral centerline 110. The term "longitudinal", as used herein, refers to a line, axis, or direction in the plane of the diaper 20 that is generally aligned with (e.g. approximately parallel with) a vertical plane which bisects the diaper 20 on a standing wearer into left and right halves. The terms "lateral" and "transverse", as used herein, are interchangeable and refer to a line, axis or direction in the plane of the diaper 20 that is generally perpendicular to the longitudinal centerline and which divides the diaper into front and rear halves. The longitudinal direction is defined as the direction perpendicular to the transverse centerline 110. The lateral direction is defined as the direction perpendicular to the longitudinal centerline 100.

The absorbent core 26 may be any absorbent member which is generally compressible, conformable, non-irritating to the wearer's skin, and capable of absorbing and retaining liquids such as urine and other certain body exudates. As shown in FIG. 1, the absorbent core 26 has a pair of side edges designated 46, a first core end edge 47 disposed in the first waist region 36 and a second core end edge 48 disposed in the second waist region 38. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including conform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 26 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 26 may also be varied to accommodate wearers ranging from infants through adults. However, the total absorbent capacity of the absorbent core 26 should be compatible with the design loading and the intended use of the diaper 20.

The absorbent core 26 may be joined with the topsheet 22, the backsheet 24, or both in any manner as is known in the art. However, embodiments of the present invention are envisioned wherein portions or the entire core 26 is unattached to either the topsheet 22, the backsheet 24, or both. Further, the absorbent core 26 may take on any size or shape that is compatible with the diaper 20. One preferred embodiment of the diaper 20 has an asymmetric, modified T-shaped absorbent core 26 having ears in the first waist region but a generally rectangular shape in the second waist region. Exemplary absorbent structures for use as the absorbent core 26 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 24 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 24 prevents the exudates absorbed and contained in the absorbent core 26 from wetting articles which contact the diaper 20 such as bedsheets and undergarments, however, the backsheet 24 may permit vapors to escape from the absorbent core 26 (i.e., is breathable). Thus, the backsheet 24 preferably comprises a woven or nonwoven material, polymeric films such as thermoplastic films of polyethylene or polypropylene, or composite materials such as a film-coated nonwoven material. A suitable backsheet 24 is a thermoplastic film having a thickness of from about 0.012 mm (0.5 mil) to about 0.051 mm (2.0 mils). Preferably, the backsheet 24 is embossed and/or matte finished to provide a more clothlike appearance.

In preferred embodiments of the present invention, at least a portion of the backsheet 24 is subjected to mechanical stretching in order to provide both a "zero strain" stretch laminate that forms the side panels 30 or to prestrain any portion of the backsheet 24 including, but not limited to, those portions coinciding with the waist features 32 and 34. The backsheet 24 can be prestrained by directing the backsheet through an incremental mechanical stretching system similar to the operation described with respect to the formation of the "zero strain" stretch laminate backsheet and elasticized side panels in U.S. Pat. No. 5,151,092 entitled "Absorbent Article With Dynamic Elastic Waist Feature Having A Predisposed Resilient Flexural Hinge", issued to Buell et al., on Sep. 29, 1992, and U.S Pat. No. 5,330,458 entitled "Absorbent Article With Elastic Feature Having A Portion Mechanically Prestrained", issued to Buell et al. on Jul. 19, 1994; which patents are herein incorporated by reference. Accordingly, the backsheet is preferably elongatable, more preferably drawable, but not necessarily elastomeric, so that the backsheet 24 will, upon mechanical stretching, be at least to a degree permanently elongated such that it will not fully return to its original undistorted configuration. In preferred embodiments, the backsheet 24 can be subjected to mechanical stretching without undue rupturing or tearing. Thus, it is preferred that the backsheet 24 have an ultimate elongation to break of at least 400% to about 700% in the cross-machine direction as measured using a method consistent with ASTM (American Society of Testing Materials) D-638. Films suitable for use as the backsheet 24 generally contain a high content of linear low density polyethylene. The Clopay Corporation of Cincinnati, Ohio, manufactures a suitable backsheet under the designation 1401. Other suitable materials for the backsheet 24 include RR8220 blown films and RR5475 cast films as manufactured by Tredegar Industries, Inc. of Terre Haute, Ind.

Alternatively, the backsheet 24 or portions of the backsheet 24 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the co-pending, commonly assigned U.S. patent application Ser. No. 08/203,456 entitled "Absorbent Article with Multiple Zone Structural Elastic-Like Film Web Extensible Waist Feature" filed by Donald C. Roe, et al. on Feb. 24, 1994, which is incorporated herein by reference.

The size of the backsheet 24 is dictated by the size of the absorbent core 26 and the exact diaper design selected. In a preferred embodiment, the backsheet 24 has a modified hourglass shape extending beyond the absorbent core a minimum distance of about 1.3 cm to about 6.4 cm (about 0.5 to about 2.5 inch) around the entire diaper periphery.

The topsheet 22 is preferably compliant, soft feeling, and non-irritating to the wearer's skin. Further, the topsheet 22 is preferably liquid pervious permitting liquids (e.g., urine) to readily penetrate through its thickness. A suitable topsheet 22 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 22 is preferably made of a hydrophobic material to isolate the wearer's skin from liquids which have passed through the topsheet 22 and are contained in the absorbent core 26 (i.e. to prevent rewet). If the topsheet 22 is made of a hydrophobic material, at least the upper surface of the topsheet 22 is treated to be hydrophilic so that liquids will transfer through the topsheet more rapidly. This diminishes the likelihood that body exudates will flow off the topsheet 22 rather than being drawn through the topsheet 24 and being absorbed by the absorbent core 26. The topsheet 22 can be rendered hydrophilic by treating it with a surfactant. Suitable methods for treating the topsheet 22 with a surfactant include spraying the topsheet 22 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of the present invention, at least a portion of the topsheet 22 is subjected to mechanical stretching in order to provide a "zero strain" stretch laminate that forms the side panels 30 or to prestrain any portion of the topsheet 22 coinciding with the waist features 32 and 34. The topsheet 22 can be prestrained by any methods as are known in the art including, but not limited to, the methods described herein with respect to the formation of the "zero strain" stretch backsheet. Thus, the topsheet 22 is preferably elongatable, more preferably drawable, but not necessarily elastomeric, so that the topsheet 22 will, upon mechanical stretching, be at least to a degree permanently elongated such that it will not fully return to its original configuration. In preferred embodiments, the topsheet 22 can be subjected to mechanical stretching without undue rupture or tearing. Thus, it is preferred that the topsheet 22 have a low cross-machine direction (lateral direction) yield strength.

There are a number of manufacturing techniques which may be used to manufacture the topsheet 22. For example, the topsheet 22 may be a nonwoven web of fibers. When the topsheet 22 comprises a nonwoven web, the web may be spunbonded, carded, wet-laid, melt-blown, hydroentangled, combinations of the above, or the like. A suitable topsheet 22 is carded and thermally bonded by means well known to those skilled in the fabrics art. A satisfactory topsheet 22 comprises staple length polypropylene fibers having a denier of about 2.2 As used herein, the term "staple length fibers" refers to those fibers having a length of at least about 15.9 mm (0.625 inches). Preferably, the topsheet 22 has a basis weight from about 14 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 28 for providing improved containment of liquids and other body exudates. Each elasticized leg cuff 28 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. Each of these patents are incorporated herein by reference. While each elasticized leg cuff 28 may be configured so as to be similar to any of the leg bands, side flaps, barrier cuffs, or elastic cuffs described above, each elasticized leg cuff 28 preferably comprises a gasketing cuff as described in the above-referenced U.S. Pat. No. 3,860,003 and a barrier cuff as described in the above-referenced U.S. Pat. No. 4,909,803.

The diaper 20 preferably further comprises side panels 30 extending laterally outwardly from the side edges 46 of the absorbent core 26 in the second waist region. The side panels 30 may be formed from extensions of the topsheet 22, the backsheet 24, or both, or may be separate members joined to the diaper 20. Examples of suitable side panels are described in U.S. Pat. No. 5,242,436 entitled "Absorbent Article With Fastening System Providing Dynamic Elasticized Fit" issued to Weil et al. on Sep. 7, 1993; and U.S. patent application Ser. No. 08/155,048 entitled "Absorbent Article With Multi-directional Extensible Side Panels", filed on Nov. 19, 1993 in the names of Robles et al.. In a preferred embodiment, at least a portion of each side panel 30 is elastically extensible. (As used herein, the terms "elastically extensible" and "elastomeric" refer to materials that extend in at least one direction, while offering some resistance to extension, when a force is applied and return approximately to their original dimensions after the force is removed.) Suitable materials for use as, or in the side panels 30 include structural elastic-like film (SELF) webs, as described above, synthetic or natural rubber, synthetic or natural rubber foams, elastomeric scrims, woven and nonwoven elastomeric webs, elastomeric composites such as nonwoven laminates, zero strain stretch laminates, prestrained stretch laminates or the like. U.S. Pat. No. 5,151,092 describes suitable zero strain stretch laminates and prestrained stretch laminates, and is herein incorporated by reference.

Figure 4:
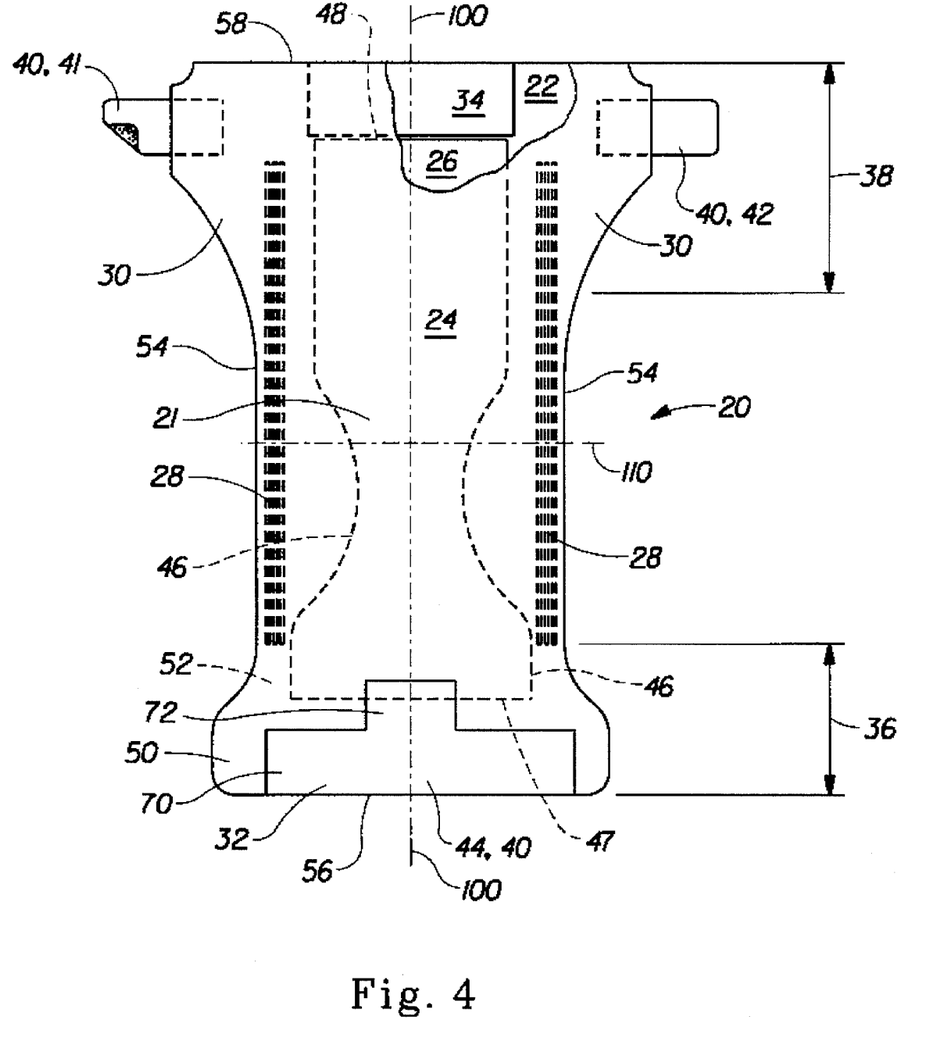
FIG. 4 is a plan view of an alternative disposable diaper embodiment of the present invention having portions cut away to reveal underlying structure, the outer surface of the diaper faces the viewer.

As shown in FIG. 1 preferred embodiments of the present invention comprise elastically extensible waist features, first waist feature 32 disposed adjacent the diaper's 20 first end edge 56 in the first waist region 36, and second waist feature 34 disposed adjacent the diaper's 20 second end edge 58 in the second waist region 38. The waist features 32 and 34 may be of any size and shape that is compatible with the design of the diaper 20. Thus, the waist features 32 and 34 may make up the entire first and second waist regions 36 and 38, respectively, or may form any portions thereof. Referring to FIG. 4, in one alternative embodiment, the first waist feature 32 may be somewhat "T-shaped". In this configuration there is a first laterally extensible portion 70 having a first width taken in the lateral direction and a second laterally extensible portion 72 disposed longitudinally inboard of the first portion 70. The second portion has a second width taken in the lateral direction which is less than the first width. This arrangement provides the advantages of additional extensibility to accomodate the stomach bulge of the wearer.

The waist features 32 and 34 may comprise separate elements affixed to the containment assembly 21 of the diaper 20 or may comprise extensions of other elements of the diaper 20 such as the topsheet 22, the backsheet 24, or both. Further, the waist features 32 and 34 may be constructed of a number of different materials, including but not limited to those described with regard to the topsheet 22, the backsheet 24 or side panels 30. In other preferred embodiments, the waist features 32 and 34 may comprise elastomeric materials interposed between the topsheet 22 and the backsheet 24 and joined with either the topsheet 22 or the backsheet 24. Examples of a suitable waist features are described in U.S. Pat. No. 4,515,595 entitled "Disposable Diapers With Elastically Contractible Waistbands", issued to Kievit and Osterhage on May 7, 1985; U.S. Pat. No. 5,151,092 issued to Buell et al. on Sep. 29, 1992; and U.S. Pat. No. 5,330,458 entitled "Absorbent Article With Elastic Feature Having A Portion Mechanically Prestrained", issued to Buell et al. on Jul. 19, 1994. Examples of nonwoven female components for a refastenable fastening device that may be suitable for use as an extensible waist feature are described in co-pending U.S. patent application Ser. No. 08/254,814 entitled "Nonwoven Female component For Refastenable Fastening Device and Method of Making the Same" filed on Jun. 6, 1994 in the name of Patrick Jay Allen et al; and U.S. patent application Ser. No. 08/287,571 entitled Nonwoven Female Component For Refastenable Fastening Device" filed on Aug. 8, 1994 in the names of King, et al.. Each of these patents and patent applications is hereby incorporated herein by reference.

The waist features 32 and 34 may comprise materials that have been "prestrained", or "mechanically prestrained" (i.e. subjected to some degree of localized pattern mechanical stretching to permanently elongate the material), or structure elastic-like webs (SELF), as described above. The materials used in the waist features 32 and 34 may be prestrained using deep embossing techniques as are known in the art. Alternatively, the materials may be prestrained by directing the materials through an incremental mechanical stretching system as described in U.S. Pat. No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

As shown in FIG. 1, the absorbent article of the present invention further comprises a fastening system 40. The fastening system 40 comprises a pair of engaging components 41 and 42, each of which are preferably disposed in the second waist region 38. In especially preferred embodiments of the present invention, the engaging components 41 and 42 are disposed on laterally opposed side panels 30.

Fastening system 40 further comprises a landing component 44 preferably disposed in the first waist region 36. (It should be noted that the term "landing component" is not limited to a single member, therefore, the landing component may comprise any number of discrete separate members.) The landing component 44 is preferably disposed on the outer surface 50 of the absorbent article and are preferably engageable with the engaging components 41 and 42. The landing component 44 is preferably longitudinally registered with, and at least partially coincident with said first waist feature 32 in said first waist region 36. (As used herein, the term "longitudinally registered" means that at least a portion of the members that are longitudinally registered are located the same distance in the longitudinal direction from the intersection of the longitudinal centerline 100 and the lateral centerline 110 of the absorbent article. The term "laterally registered" means that at least a portion of the members that are laterally registered are located the same distance in the lateral direction from the intersection of the longitudinal centerline 100 and the lateral centerline 110 of the absorbent article. The term "coincident" means that the members are at least partially laterally and longitudinally registered with each other, or integral with each other. The term "integral" means joined to another member and neither divided nor discontinuous with the other member.) Thus, at least a portion of the landing component 44 is located the same longitudinal distance from the intersection of the longitudinal centerline 100 and the lateral centerline 110 as the first waist feature 32. Further, at least a portion of the landing component 44 overlaps or is integral with the first waist region 36. This ensures that the tensional forces imposed on the landing component 44, the second waist feature 34, or either of the side panels 30, when the diaper 20 is fitted to the wearer, activates the first waist feature 32. (As used herein, the term "activates" means to apply a force to an elastically extensible member in a relaxed condition such that the elastically extensible member is extended such that it is no longer in the relaxed condition and thus, may expand and contract with the subsequent application and removal of forces.) Thus, the first waist feature 32 provides the diaper 20 with a snug yet comfortable fit about the waist of the wearer.

Activation of the first waist feature 32 can be achieved by directly providing tension to the first waist feature 32 or by tensioning the side panels 30 and/or the second waist feature 34. To activate the first waist feature 32 directly, a diaperer fitting the diaper to a wearer provides lateral tension on the first waist feature 32, extending the first waist feature 32, before fastening of the diaper 20 about the wearer is completed. (The diaper 20 is fastened about the waist of the wearer by engaging the engaging components 41 and 42 with the landing component 44.) Thus, the activated first waist feature 32 can provide a sustained conforming fit in the waist region of the wearer.

Alternatively, if either or both of the side panels 30 and/or the second waist feature 34 are activated, the side panels 30 and/or the second waist feature 34 can store the energy provided by the diaperer until the diaperer releases the tension on the side panels 30 after the diaper 20 has been fastened about the wearer. Once the diaper 20 has been fastened about the waist of the wearer, the energy stored in the activated side panels 30 and/or second waist feature 34 is transferred to the first waist feature 32 providing tension directed outwardly in the lateral direction. Thus, the first waist feature 32 becomes activated and provides a sustained conforming fit in the waist region of the wearer.

The fastening system 40 can comprise any attachment means known in the art including pressure sensitive adhesives, cohesive materials, mechanical fasteners such as hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu and Robertson on May 5, 1987. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; U.S. Pat. No. 4,846,815 entitled "Disposable Diaper Having an Improved Fastening Device" issued to Scripps on Jul. 11, 1989; and U.S. Pat. No. 5,151,092 entitled "Absorbent Article With Dynamic Elastic Waist Feature Having A Predisposed Resilient Hinge", issued to Buell et al., on Sep. 29, 1992. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

One embodiment of the present invention comprises a hook fastening material preferably comprising a base and a plurality of engaging elements extending from the base. The hook fastening material is intended to engage fibrous elements of a loop fastening material so as to provide a secure fastening device. It should also be understood however, that the use of the term "hook" should be non-limiting in the sense that the engaging elements may comprise any shapes as are known in the art so long as they are adapted to engage a complementary landing component. The hook fastening material may be manufactured from a wide range of materials. Suitable materials include nylon, polyester, polypropylene, or any combination of these materials. A suitable hook fastening material comprises a number of shaped engaging elements projecting from a woven backing such as the commercially available material designated "SCOTCHMATE" brand No. FJ3402 available from Minnesota Mining and Manufacturing Company, St. Paul, Minn. Alternatively, the engaging components may comprise "T" shaped engaging elements, as supplied by Aplix, Inc. of Charlo6tte, N.C. under the designations 942B and 957D, or any other shapes as are well known in the art. Other preferred hook fastening components are described in U.S. Pat. No. 5,058,247 entitled "Mechanical Fastening Prong" issued to Thomas Oct. 22, 1991; U.S. Pat. No. 5,116,563 entitled "Process for Producing a Mechanical Fastener" issued to Thomas et al., on May 26, 1992; U.S. Pat. No. 5,180,534 entitled "Process of Manufacturing A Refastenable Mechanical Fastening System" issued to Thomas, et al., on Jan. 19, 1993; and U.S. Pat. No. 5,230,851 entitled "Process of Manufacturing a Refastenable Fastening System" issued to Thomas on Jul. 27, 1993. Each of these patents are hereby incorporated by reference herein.

The landing component 44 preferably comprises a fastening component engageable with the engaging component 42. Thus, the landing component may be manufactured from a wide range of materials and configurations capable of securely engaging the hook component. For example, the landing component may comprise identical complementary elements or distinct complementary elements. As used herein, the term "identical complementary elements" is used to define mechanical fastening systems wherein the engaging elements of the hook component and the landing component comprise the same configuration or structure that are interlocking. Examples of such systems are described in Brown et al. U.S. Pat. No. 4,322,875 entitled "Two Strip Materials Used For Forming Fasteners" issued on Apr. 16, 1982 and Kellenberger et al. U.S. Pat. No. 4,701,179 entitled "Fixed Position Fasteners For Disposable Absorbent Garments" issued on Oct. 20, 1987. The term "distinct complementary elements" is used herein to designate a system wherein the hook component is different from the landing component but is engageable therewith.

In one preferred embodiment, the landing component 44 comprises a plurality of fiber elements, such as a loop fastening material, that engage the engaging elements of the hook component. The loop fastening material may be manufactured from a wide range of materials to provide fiber elements, preferably loops. Suitable materials include nylon, polyester, polypropylene, or any combination of these materials. A suitable loop fastening material comprises a number of fiber loops projecting from a woven backing such as the commercially available material designated "SCOTCHMATE" brand nylon woven loop No. SJ3401 available from Minnesota Mining and Manufacturing Company, St. Paul, Minn. A preferred loop fastening material comprises a tricot knit fabric having a plurality of nylon filament loops projecting from a backing of nylon such as the commercially available material designated "Guilford No. 18904" available from Guilford Mills of Greensboro, N.C. Alternatively, the loop fastening material may be a non-woven fabric or any other type of fiber material or loop material which are well known in the art. Inexpensive loop fastening materials and a methods of making the same are described in U.S. Pat. No. 5,032,122, entitled "Loop Fastening Material For Fastening Device and Method of Making Same" issued to Noel et al., Jul. 16, 1991; U.S. Pat. No. 5,326,612, entitled "Nonwoven Female Component For Refastenable Fastening Device And Method Of Making The Same" issued to Goulait on Jul. 5, 1994; PCT WO 92/20250 entitled "Multilayer Female Component For Refastenable Fastening Device And Method Of Making The Same", assigned to The Procter & Gamble Company and published on Nov. 26, 1992; co-pending U.S. patent application Ser. No. 08/254,814 entitled "Nonwoven Female component For Refastenable Fastening Device and Method of Making the Same" filed on Jun. 6, 1994 in the name of Patrick Jay Allen et al.; and U.S. patent application Ser. No. 08/287,571 entitled Nonwoven Female Component For Refastenable Fastening Device" filed on Aug. 8, 1994 in the names of King, et al., all of which are incorporated herein by reference.

Figure 2:
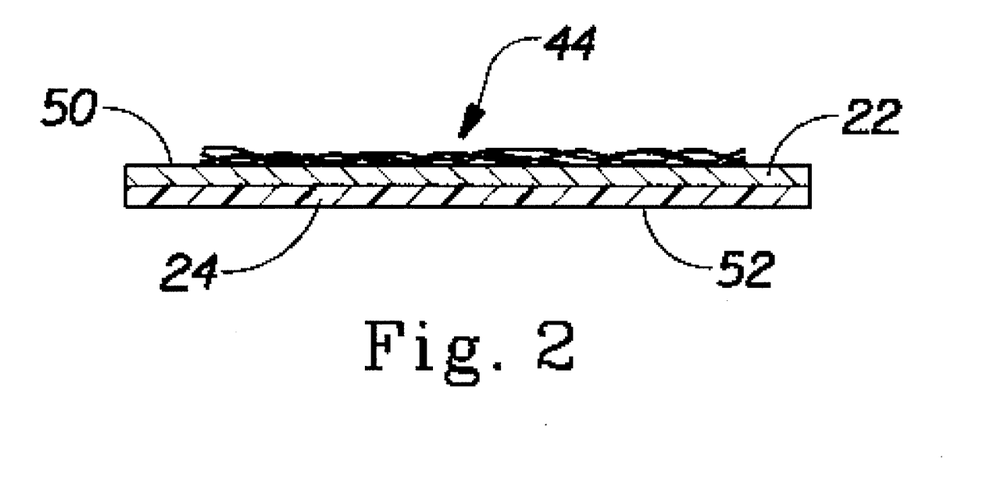
FIG. 2 is a fragmentary, cross-sectional view of one embodiment of the diaper shown in FIG. 1 taken through section line 2—2.
Figure 3:
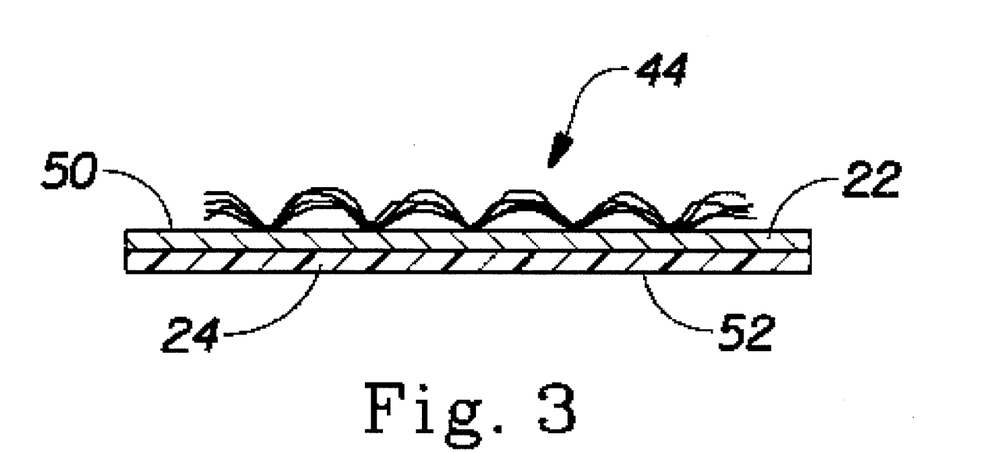
FIG. 3 is a fragmentary, cross-sectional view of one embodiment of the diaper shown in FIG. 1 in a contracted state.

The landing component 44, and the engaging components 41 and 42 may be disposed on either the outer surface 50 (as shown in FIGS. 2 and 3) or the inner surface 52 of the diaper 20. In preferred embodiments, however, the fastening components are disposed on the diaper 20 such that the fastening system 40 does not irritate the skin of the wearer. Accordingly, any fastening components that are disposed on the inner surface 52 are preferably soft and non-irritating. In addition, the fastening components may either be discrete separate elements joined to the diaper 20 (i.e. tape tabs), or integral with any element of the diaper 20, such as the topsheet 22 or the backsheet 24.

The diaper 20 is preferably applied to a wearer by positioning one of the waist regions, preferably the second waist region 38, under the wearer's back and drawing the remainder of the diaper 20 between the wearer's legs so that the other waist region, preferably the first waist region 36, is positioned across the front of the wearer. The diaperer then wraps the side panels 30 about the wearer. The elastically extensible side panels 30, or second waist feature 34, or both will typically be extended and tensioned during this operation. The force applied to extend and tension the side panels 30 and/or the second waist feature 34 is stored in the elastically extensible portion of the side panels 30 and/or the second waist feature 34 until the diaperer releases the force. Typically, the diaperer will release the force applied to the side panels 30 once the diaper 20 has been fastened about the waist of the wearer. Preferably the diaperer utilizes the fastening system to effect closures on each side of the diaper 20 by engaging the engaging components with the landing component 44. The energy stored in the elastically extensible portions of the side panels 30 and/or the second waist feature 34 is transferred to the first waist feature 32 when the diaperer releases the tension applied to the side panels 30. The transfer of energy from the side panels 30 and/or second waist feature 34 activates the first waist feature 32 permitting the first waist feature 32 to expand and contract with the motions of the wearer. Alternatively, the first waist feature 32 may be directly activated by the diaperer. To activate the first waist feature 32 directly, the diaperer stretches the first waist feature prior to engaging one or both of the engaging components 41 and 43. Thus, a waistband and fastening system is provided that improves the sustained dynamic fit of the diaper 20.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article to be fitted to a wearer, the absorbent article comprising:

(a) a containment assembly comprising a topsheet and a liquid impervious backsheet joined with said topsheet, said containment assembly having a longitudinal centerline, a longitudinal direction which is the direction parallel to said longitudinal centerline, a lateral centerline, a lateral direction which is the direction parallel to said lateral centerline, a first waist region, a first waist feature positioned in said first waist region and being elastically extensible in said lateral direction, said first waist feature comprising a first lateral extensible portion having a first width taken in the lateral direction and a second laterally extensible portion disposed longitudinally inboard of said first laterally extensible portion, said second portion having a second width taken in said lateral direction which is less than said first width, a second waist region longitudinally opposed to said first waist region, a first end edge, a second end edge, an inner surface, an outer surface and a pair of longitudinal edges;

(b) a fastening system comprising:
      (i) a pair of engaging components disposed in said second waist region; and
      (ii) a continuous landing component disposed on said outer surface of the absorbent article in said first waist region coincident with said first waist feature, said landing component being engageable with said engaging components; said landing component being elastically extensible in at least said lateral direction and at least a portion of said landing component being intermediate said engaging components when said engaging components are engaged with said landing component such that said first waist feature and said landing component are activated when the absorbent article is fitted to said wearer; and (c) a pair of elastically extensible side panels disposed in said second waist region, one of said side panels extending laterally outwardly from each of said longitudinal edges of said containment assembly, said side panels being elastically extensible in at least said lateral direction.

2. The absorbent article of claim 1 wherein said containment assembly further comprises an absorbent core positioned between said topsheet and said backsheet.

3. The absorbent article of claim 2 further comprising a pair of elastically extensible side panels disposed in said second waist region, one of said side panels extending laterally outwardly from each of said longitudinal edges of said containment assembly, said side panels being elastically extensible in at least said lateral direction.

4. The absorbent article of claim 3 wherein one of said engaging components is disposed on each of said side panels.

5. The absorbent article of claims 2, 3 or 4 further comprising a second waist feature disposed in said second waist region, at least a portion of said second waist feature being elastically extensible in at least said lateral direction.

6. The absorbent article of claims 2, 3 or 4 wherein said first waist feature at least partially overlaps said absorbent core.

7. The absorbent article of claims 2, 3 or 4 wherein said first waist feature is integral with said containment assembly.

8. The absorbent article of claims 2, 3 or 4 wherein said elastically extensible portion of said first waist region comprises a separate, elastically extensible member that is joined with said containment assembly.

9. The absorbent article of claims 2, 3 or 4 wherein said landing component comprises the loop component of a hook and loop fastener and said engaging components comprise the hook components of a hook and loop fastener.

* * * * *